United States Patent
Kato et al.

(10) Patent No.: US 6,787,518 B1
(45) Date of Patent: Sep. 7, 2004

(54) THERAPEUTICS OF OSTEOARTHRITIS AND INFLAMMATORY JOINT DISEASE

(76) Inventors: Yukio Kato, 3-6-9-501, Ushitawaseda, Higashi-ku, Hiroshima-shi, Hiroshima-ken (JP); Masahiro Iwamoto, 4-6-10-606, Aoshinke, Minoo-shi, Osaka 562 (JP); Tatsuya Koike, 26-16, Kariyaminamimachi, Shijonawate-shi, Osaka 575 (JP)

( * ) Notice: Subject to any disclaimer, the term of this patent is extended or adjusted under 35 U.S.C. 154(b) by 0 days.

(21) Appl. No.: 08/894,443

(22) PCT Filed: Feb. 19, 1996

(86) PCT No.: PCT/JP96/00362

§ 371 (c)(1),
(2), (4) Date: Aug. 19, 1997

(87) PCT Pub. No.: WO96/25944

PCT Pub. Date: Aug. 29, 1996

(30) Foreign Application Priority Data

Feb. 20, 1995 (JP) ............................................. 7-030803

(51) Int. Cl.⁷ .............................................. A61K 38/29
(52) U.S. Cl. ............................. 514/2; 514/12; 514/825; 530/324; 530/399
(58) Field of Search ................................ 530/300, 324, 530/350, 399; 424/198.1; 514/2, 12, 825

(56) References Cited

U.S. PATENT DOCUMENTS 5,747,456 A  *  5/1998  Chorev et al. ................. 514/12

FOREIGN PATENT DOCUMENTS

| EP | 451867 | 10/1991 |
|---|---|---|
| WO | 8809376 | 12/1988 |
| WO | 9408613 | 4/1994 |

OTHER PUBLICATIONS

Funk, et al. J. Clin Inv 101 (7) pp 1362–1371, Apr. 1998.*
Kohno, et al J of Bone and Mineral Res 12(5) pp 847–854, May 1997.*
Ngo et al., Chapter 14, from: "The Protein Folding Problem and Tertiary Structure Predicition", Ed. Merz et al., Birkhauser, 1994, pp. 492–495.*
Akatsu et al., Parathyroid hormone (PTH)–related protein is a potent stimulator of osteoclast–like multinucleated cell formation to the same extent as PTH in mouse marrow cultures, Endocrinolgy, vol. 125 (1), pp. 20–27, 1989.*
Chatterjee et al, Cancer Immunol. Immunother. vol. 38, pp. 75–82, 1994.*
Karaplis, A.C., et al., "Lethal Skeletal Dysplasia from Targeted Disruption of the Parathyroid Hormonerelated Peptide Gene," *Genes and Development* 8:277–289 (1994).
Suva, L.J., et al., "A Parathyroid Hormone–Related Protein Implicated in Malignant Hypercalcemia: Cloning and Expession," *Science* 273:893–896 (1987).
Abstract of WO 95 11697, 1995.

* cited by examiner

*Primary Examiner*—David Saunders
(74) *Attorney, Agent, or Firm*—Browdy and Neimark, P.L.L.C.

(57) ABSTRACT

Drugs for preventing or treating diseases that involve the destruction and degeneration of articular cartilage tissue contain a parathyroid hormone related peptide (PTHrP) or a PTHrP derived substance as an effective ingredient.

6 Claims, 6 Drawing Sheets

US 6,787,518 B1

THERAPEUTICS OF OSTEOARTHRITIS AND INFLAMMATORY JOINT DISEASE

This application constitute a U.S. patent application under 35 USC 371 of PCT/JP96/00362 filing date Feb. 19, 1996.

TECHNICAL FIELD

This invention relates to drugs having either preventive or therapeutic effect on osteoarthritis and other diseases that involve the destruction and degeneration of the articular cartilage tissue.

BACKGROUND ART

Osteoarthritis involves the collapse of the articular cartilage surface and the resulting growth of new cartilage at the articular margins, joint deformity and loss of compliance, which are eventually manifested as the inflammation of the synovial membrane of the joint. Osteoarthritis is divided into two types, primary and secondary. Secondary osteoarthritis has predisposing causes such as trauma and infection that lead to the degeneration of cartilage but no predisposing cause can be identified in primary osteoarthritis. The principal lesion of osteoarthritis is the degeneration of articular cartilage and it may be attributable to the endogenous degeneration of articular cartilage and the mechanical stress on the joint; however, the mechanism of its etiology remains unknown in many aspects. Two major pathological phenomena occur in osteoarthritis. In one case, accelerated calcification of subchondral bone causes narrowing of joint fissures and destruction of the bone tissue (Bollet, A. J., Arthritis Rheum. 12, 152–163, 1969); in the other case, synovial inflammation causes either destruction or degeneration of the cartilaginous tissue (Huskisson, R. C. et al., Ann. Rheum. Dis. 38, 423–428, 1979; Campion, G. V. et al., Seimnars in Arthritis and Rheumatism 17, 232–245, 1988).

In inflammatory osteoarthritis, an observable decrease of proteoglycans (a matrix component of cartilaginous tissue) occurs due to such substances as IL-1 produced as from the synovial tissue (Tyler, J. A., Biochem. J. 225, 493–507, 1985); in addition, the production of proteoglycans by chondrocytes is suppressed (Ratcliffe, A., Biochem. J. 238, 571–580, 1986). As a result, the cartilage matrix would decrease (Pettipher, E. R. et al., Proc. Natl. Acad. Sci. USA 83, 8749–8753, 1986) to cause gradual loss of the articular cartilage layer.

The cartilage in the Joint tissue is classified as a permanent cartilage which is strictly distinguished from a grown cartilage which plays an important role in skeletal growth. Grown chondrocytes typically occurring in epiphysial cartilage plate go through the stages of growth, differentiation and calcification until they are replaced by bone, whereupon they fulfill their physiological function. In contrast, articular cartilage cells do not normally become calcified; this is because environmentally, calcification is strongly restrained from occurring in articular cartilage cells and because it is not calcified, the articular cartilage retains elasticity to thereby serve as a load-bearing cushion and assure high mobility at the joint. However, the elasticity of the articular cartilage surface is known to decrease in osteoarthritis (Myers, E. R. et al., Trans. Orthop. Res. USA 231, 1986). This is believed to be attributable to the rupturing of collagen fibers in the cartilaginous tissue (Stockwell, R. A. et al., J. Anat. 136, 425–439, 1982). The mechanism by which calcification is suppressed in the articular cartilage is not clear but calcification does take place when isolated articular cartilage cells are cultivated. Most probably, the strong suppressor of calcification of articular cartilage exists within the matrix surrounding the chondrocytes (Iwamoto, M. et al, J. Biol. Chem. 266, 461–467, 1991; Pacifici, M. et al., Exp. Cell Res. 192, 266–270, 1991).

Other differences can be found between the calcifying chondrocytes and the articular artilage cells. The calcifying cartilage hash alkaline phosphatase activity (Robinson, R., Biochem. J. 17, 286–293; 1923; Ali, S. Y., in "Cartilage" (B. K. Hall, ed.), Vol. 1, pp. 343–378, Academic Press, New York) whereas only a hundredth of that activity is exhibited by the articular cartilage tissue (Iwamoto, M. et al., J. Biol. Chem. 266, 461–467, 1991). The cartilage matrix contains type X collagen and this occurs in a calcified cartilaginous tissue (Capasso, O. et al., Exp. Cell Res., 142, 197–206, 1982) but its occurrence is limited in the articular cartilage. It has been suggested that these markers are associated with the calcification of chondrocytes (Kato, Y. et al., Proc. Natl. Acad. Sci. USA 85, 9552–9556, 1988; Kwan, A. P. L. et al., J. Cell Biol. 109, 1849–1856, 1989). In osteoarthritis, articular cartilage cells have a higher alkaline phosphatase activity than normal articular cartilage cells (Mokondjimobe, E. et al., 39, 759–762, 1991) and it has been found in a study using human articular cartilage tissue that an osteoarthritic tissue has a higher alkaline phosphatase activity (Einhorn, T. A. et al., J. Orthop. Res. 3, 160–169, 1985). Similarly, the occurrence of type X collagen has been shown to be high in the cartilaginous tissue from patients with osteoarthritis (Hoyland, J. A. et al., Bone Miner. 15, 151–164, 1991). Based on these findings, it is speculated that the calcification of the cartilaginous tissue or subchondral bone in osteoarthritis is attributable to changes in the characters of articular cartilage cells, namely, the production of alkaline phosphatase and the occurrence of type X collagen.

The currently practised therapeutic regimens against osteoarthritis are no more than nosotropic or indirect as exemplified by preservative therapy, administration of anti-inflammatory agents or hyaluronic acid, and surgical treatments and there is no established therapeutic approach that may well be described as being "etiotropic".

The purpose of the invention is to provide medicines which serve not only as preventives of osteoarthritis and other diseases that involve the destruction and degeneration of the articular cartilage tissue but also as etiotropic and direct therapeutics of such diseases.

DISCLOSURE OF INVENTION

Briefly, the present invention relates to preventives or therapeutics of diseases that involve the destruction and degeneration of the articular cartilage tissue, said preventives and therapeutics containing a PTH related peptide (PTHrP) or a PTHrP derived substance as an effective ingredient.

The parathyroid hormone related peptide (PTHrP) to be used in the invention embraces native PTHrP, PTHrP created by genetic engineering techniques and chemically synthesized PTHrP and may be exemplified by human, bovine and porcine PTHrP that are composed of 141 amino acids, with human PTHrP being preferred. The term "PTHrP derived substance" means partial peptides of the above-listed PTHrPs, as well as peptides that are obtained by partial modification of constituent amino acids of the PTHrP or partial peptides thereof through substitution, deletion or addition and which have the same activity. Examples of partial peptides of PTHrP include 1–34PTHrP, 1–84PTHrP, 3–141PTHrP, 7–141PTHrP, 35–141PTHrP, 85–141PTHrP, 107–141PTHrP, 107–140PTHrP, 1–87PTHrP, 3–87PTHrP, 7–87PTHrP, 1–111PTHrP, 3–111PTHrP and 7–111PTHrP, with human 1–34PTHrP and human 1–84PTHrP being preferred.

The 1–34PTHrP designates a partial peptide of PTHrP which is composed of 34 amino acids as counted from the N terminus of PTHrP. The number of amino acid residues to be substituted, deleted or added is not limited to any particular value as long as the activity intended by the present invention is retained. Diseases that involve the destruction and degeneration of the articular cartilage tissue include osteoarthritis and rheumatoid arthritis, with osteoarthritis being preferred.

As already mentioned, type X collagen and alkaline phosphatase are known to be critical substances that occur during calcification of cartilage or subchondral bone and suppressing the occurrence of type X collagen and the production of alkaline phosphatase is effective for the purpose of ameliorating osteoarthritis. Other findings on osteoarthritis are the lowering of the ability of articular cartilage cells to synthesize the matrix and the deformity of cartilaginous tissue by matrix decomposition; in view of this, a preferred therapeutic of osteoarthritis is a drug that does not interfere with but accelerate the synthesis of proteo-glycans which are a component of the cartilage matrix. Needless to say, the preferred drug should not cause any untoward effect on the growth and differentiation of chondrocytes such as by interfering with their growth.

The efficacy of the PTHrP in the invention against the diseases that involve the destruction and degeneration of the articular cartilage tissue can be verified by the following procedures.

The action on the growth of chondrocytes, the action on the occurrence of type X collagen which is a critical marker in the degeneration of cartilaginous tissue, alkaline phosphatase production and the ensuing calcification, as well as the action on the occurrence of type II collagen which is a cartilage matrix component can be verified by an experiment for cultivating grown chondrocytes of a young rabbit in a centrifugal tube (Kato, Y. et al., Proc. Natl. Acad. Sci. USA 85, 9552–9556, 1988; Iwamoto, M. et al., Develop. Biol. 136, 500–506, 1989) and by a system of plane cultivation of grown chondrocytes (Shimomura, Y. et al., Calcif. Tissue Res. 19, 179–187, 1975). Particularly in the case of cultivation in a centrifugal tube, cartilage cells grew and differentiated to become calcified in about 20 days (Kato, Y. et al., Proc. Natl. Sci. Acad. USA 85, 9552–9556, 1988). In addition, when articular cartilage cells were cultivated in a similar culture system, the development of high alkaline phosphatase activity was accompanied by calcification (Pacifici, M. et al., Exp. Cell Res. 192, 266–270, 1991). It is therefore understood that these cultivation systems are models useful experimental model in evaluating the efficacy of drugs against the development of abnormal characters by articular cartilage cells in osteoarthritis.

The action of PTHrP on the matrix of chondrocytes can be verified using the synthesis of cartilage matrix proteoglycans as a marker. An applicable experimental model is such that PTHrP is allowed to act on cultured chondrocytes during matrix synthesis, with the incorporation of $^{35}$S-sulfuric acid into the matrix being used as a marker.

In order to characterize the above-described actions of PTHrP, the presence of PTHrP receptors in chondrocytes must be verified. As a matter of fact, it has been shown that the presence of PTH receptors in chondrocytes is critical to the development of various actions of PTH on chondrocytes (Lee, K. et al., Endocrinology, 134, 441–450, 1994).

BEST MODE FOR CARRYING OUT THE INVENTION

Besides injections prepared by usual pharmaceutical formulation procedures for peptides, the drug of the invention may take dosage forms that are intended for achieving localization and long lasting action as by confining in microcapsules or incorporating in sheets of gel. In the case of solutions, suitable proteins or anti-sticking agents are preferably added.

The drug of the invention may be administered by various routes, such as subcutaneous, peroral, percutaneous, intrarectal and topical, with topical administration being preferred. Particularly preferred is topical application into the joint cavity or the affected site by injection.

The dose of PTHrP according to the invention varies with the disease for which it is indicated, its symptoms and the like; at a tissue level, the dose is from $10^{-20}$ to $10^{-5}$ M, preferably from $10^{-15}$ to $10^{-7}$ M.

EXAMPLES

Examples of the invention are described below. The PTHrP used in the Examples was the human 1–34PTHrP purchased from the Peptide Institute, Inc.

Example 1

In the following Examples, grown chondrocytes were separated from the subchondral bone to bone transition area of rabbits 4 weeks old from birth by the method of Shimomura et al. (Shimomura, Y. et al., Calcif. Tissue Res. 19, 179–187, 1975). The separated chondrocytes were cultivated by the method of Iwamoto et al. (Iwamoto, M. et al. Dev. Biol. 136 500–507, 1989) and the method of Kato et al. (Kato, Y. et al. Endocrinology, 127, 114–118, 1990). Stated specifically, the separated chondrocytes were suspended in an Eagle's minimum essential medium (MEM) to give a concentration of 8×10$^4$ cells/mL in the presence of 10% fetal bovine serum (FBS) and 50 μg/mL of ascorbic acid and then seeded in 1-mL portions into 15-mL plastic centrifugal tubes (Corning). After 5-min centrifugation (at 1,500 rpm), the cells were cultivated in a $CO_2$ gas incubator having a temperature setting of 37° C. Starting on the 6th day of the cultivation, medium changes were made every other day. The presence of PTHrP receptors in the chondrocytes was verified by SDS gel electrophoresis. Stated specifically, the chondrocytes cultured for 14 days were homogenized and incubated with $^{125}I$ labelled PTHrP for 5 h. The PTHrP binding to the receptors was crosslinked with DSS, solubilized with a SDS buffer solution and electrophoresed through a SDS gel. After the electrophoresis, autoradiography was performed in the usual manner. As a control, excess PTHrP, was added to prevent the binding of $^{125}I$ labelled PTHrP to the receptors and the unbound PTHrP was electrophoresed by the same procedure and subjected to autoradiography.

Figure 1:
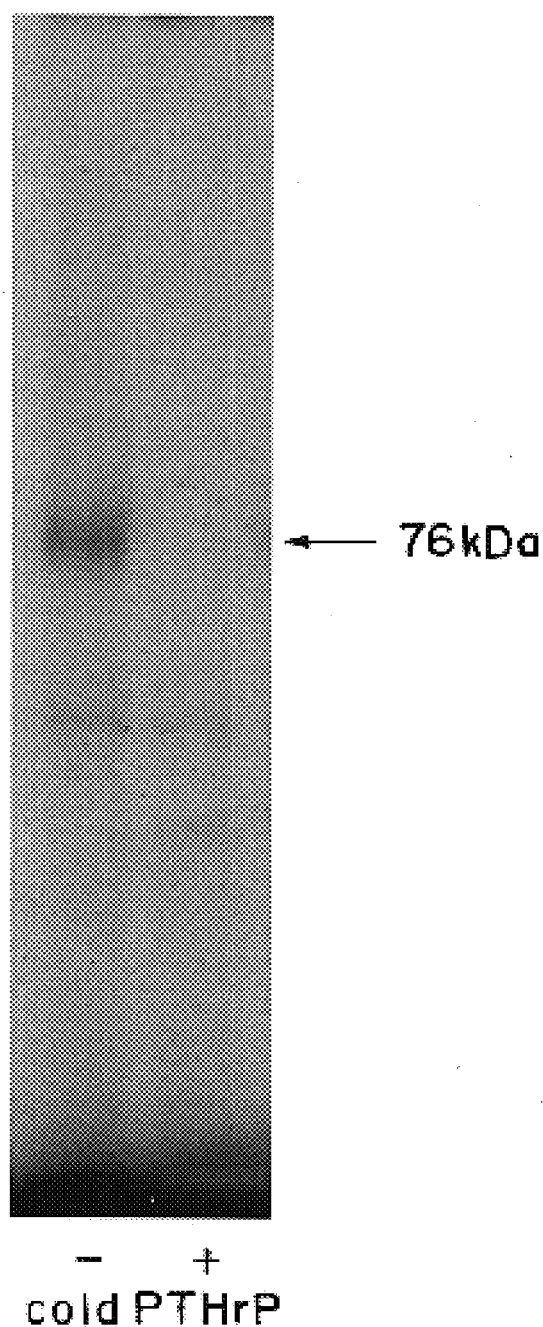
FIG. 1 is an electropherogram showing the presence of a PTHrP receptor in chondrocytes.

The results are shown in FIG. 1. The $^{125}I$ labelled PTHrP binding with the receptors electrophoresed to a site near 76 kDa in molecular weight (see the left lane in FIG. 1) and the binding was completely prevented by the addition of excess PTHrP (see the right lane in FIG. 1). This suggests the following possibilities: PTHrP receptors exist in the chondrocytes, and the intermediary of the receptors PTHrP can materialize the following effects.

Example 2

As in Example 1, grown chondrocytes were separated from the subchondral bone to bone transition area of rabbits 4 weeks old from birth by the method of Shimomura et al. (Shimomura, Y. et al., Calcif. Tissue Res. 19, 179–187, 1975). The separated chondrocytes were suspended in an Eagle's minimum essential medium (MEM) containing 10% fetal bovine serum and 50 μg/mL of ascorbic acid and seeded in a 96-well culture plate at a concentration of 5,000 cells in each well. When the cells became confluent, PTHrP was added and, one day later, 1 μCi of $^{33}S$-sulfuric acid was added per well, followed by 17-h cultivation. The amount of cartilage matrix produced in the supernatant of the culture solution was measured by the method of Kato et al. (Kato, Y. et al., Endocrinology 122, 1991–1997, 1988). Briefly, the quantity of $^{33}S$-sulfuric acid incorporated into proteoglycans was measured.

Figure 2:
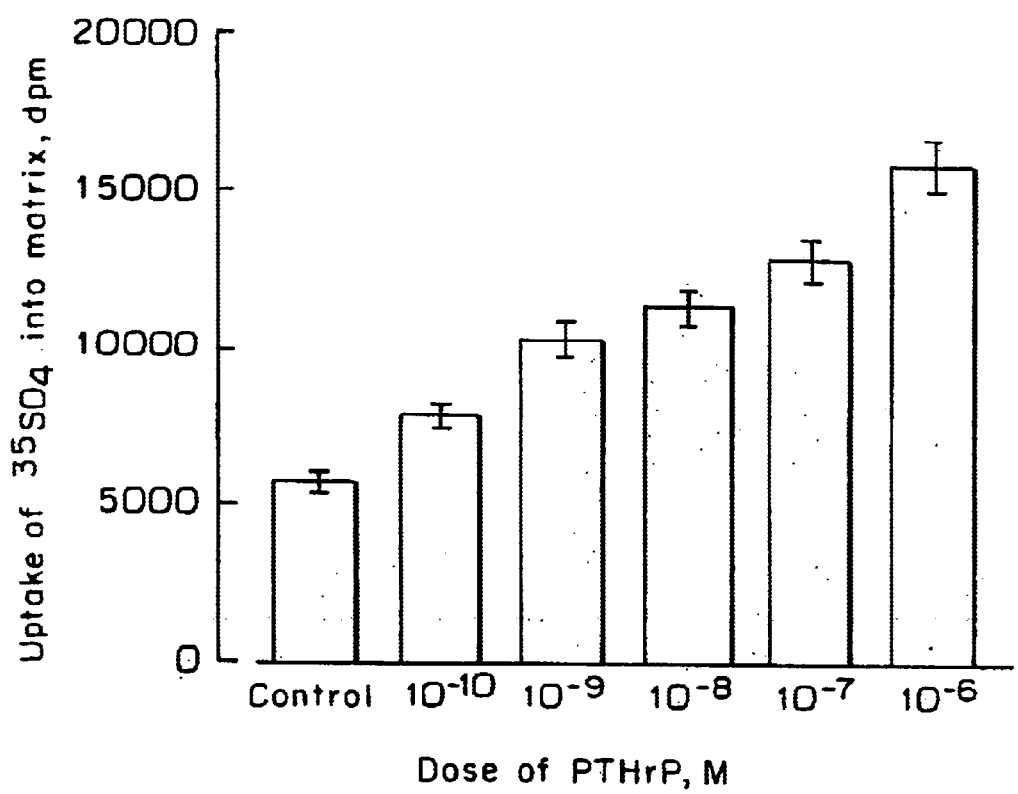
FIG. 2 is a graph showing the activity of PTHrP in promoting the synthesis of proteoglycans which are the principal component of cartilage matrix.

The results are shown in FIG. 2, which may be regarded as a dose response curve for PTHrP over the range from $10^{-10}$ to $10^{-6}$ M. Obviously, PTHrP accelerated the incorporation of $^{35}S$-sulfuric acid into proteoglycans in a dose-dependent manner and at $10^{-6}$ M, it exhibited a matrix synthesizing capability which was about 3 times as great as that of the control. This indicates the ability of PTHrP to promote proteoglycan production and, hence, the normal differentiation of chondrocytes.

Example 3

As in Example 1, chondrocytes were cultured in a centrifugal tube. On the 8th day of the cultivation, $10^{-7}$ M of PTHrP was added and the cultivation was continued for 28 days. After the cultivation, the cells were solubilized at appropriate intervals and the time-dependent changes in DNA content were measured. In another experiment, PTHrP was added at varying concentrations from $10^{-10}$ to $10^{-7}$ M and the DNA content on the 21st day of the cultivation was measured.

Figure 3:
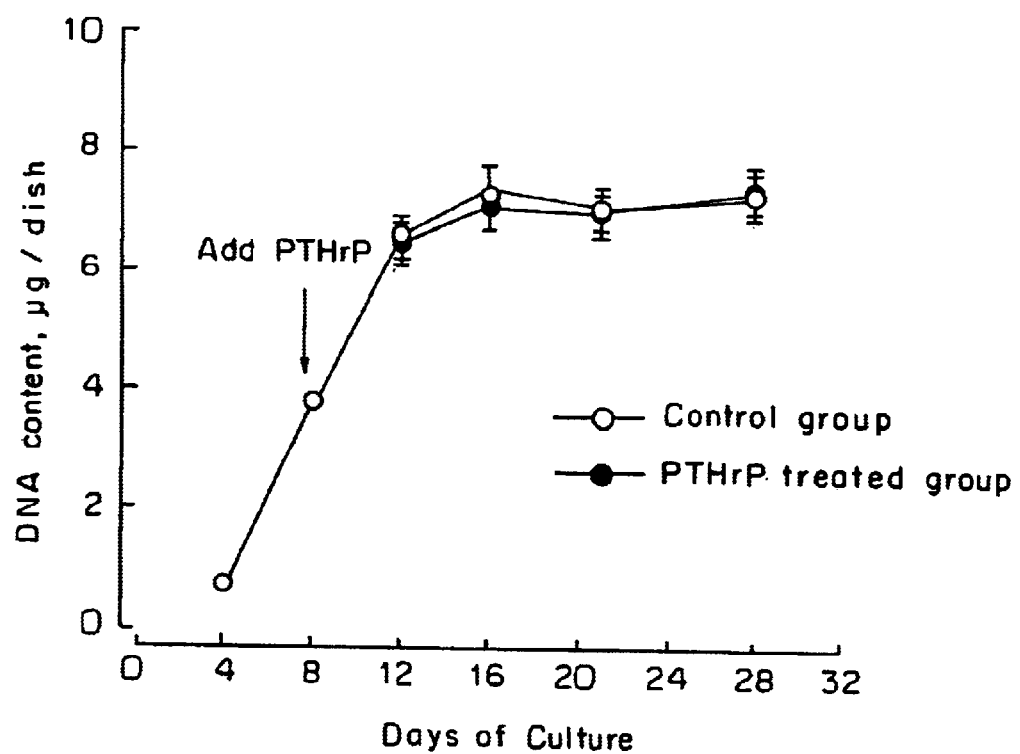
FIG. 3 is a graph showing the PTHrP action on the growth of chondrocytes.
Figure 4:
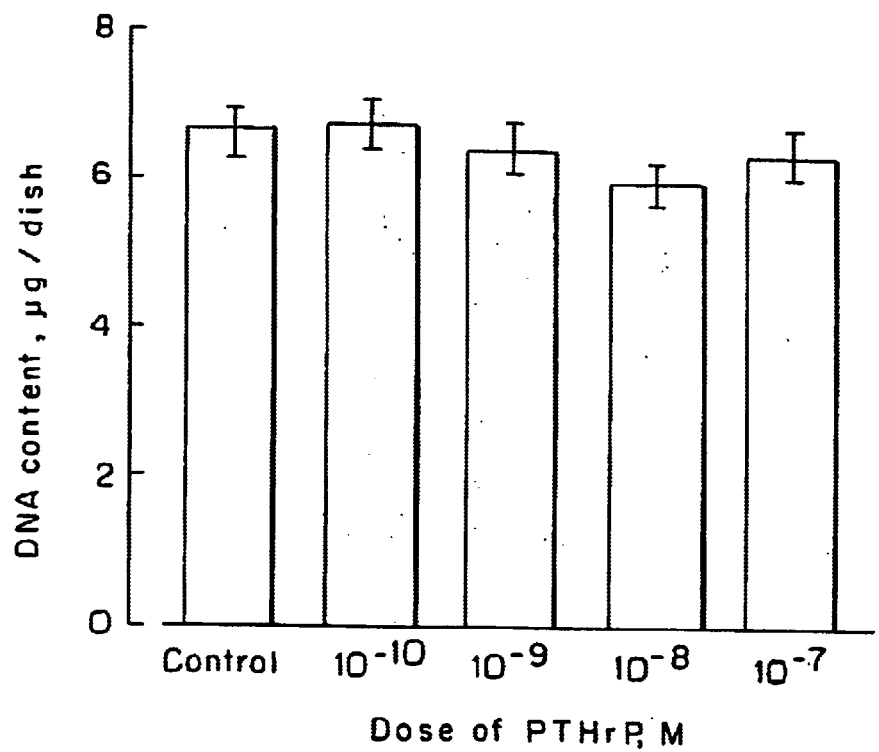
FIG. 4 is a graph showing the dose-response relationship between PTHrP and the growth of chondrocytes.

The time-dependent changes in the DNA content of the chondrocytes are shown in FIG. 3 and the dose-response relationship between PTHrP and the DNA content is shown in FIG. 4. Obviously, the DNA content of the control group increased with time, indicating satisfactory growth of chondrocytes in the centrifugal tube. The DNA content of the chondrocytes was not influenced at all by the addition of PTHrP. This shows that PTHrP is a drug that causes no adverse effects on the growth of chondrocytes.

Example 4

As in Example 1, chondrocytes were cultured in a centrifugal tube. On the 8th day of the cultivation, $10^{-7}$ M of PTHrP was added and the cultivation was continued for a period of up to 28 days. On the 21st day of the cultivation, a PTHrP free group was set and compared with the PTHrP treated group. In another experiment, PTHrP was added in varying amounts from $10^{-1}$ to $10^7$ M and the dose-response relationship with the alkaline phosphatase activity (ALP activity) was verified. For the measurement of ALP activity, chondrocyte clusters were homogenized in 0.2% Triton X-100, centrifuged at 12,000 xg for 15 min and the supernatant was assayed by the method of Bessey et al. (Bessey O. A. et al., J. Biol. Chem. 164, 321–329, 1946). To investigate the progress of calcification, 0.5 μCi of $^{45}Ca$ was added at suitable intervals and its incorporation into the chondrocytes after 24 h, as well as the Ca level on the 28th day of the cultivation were measured.

Figure 5:
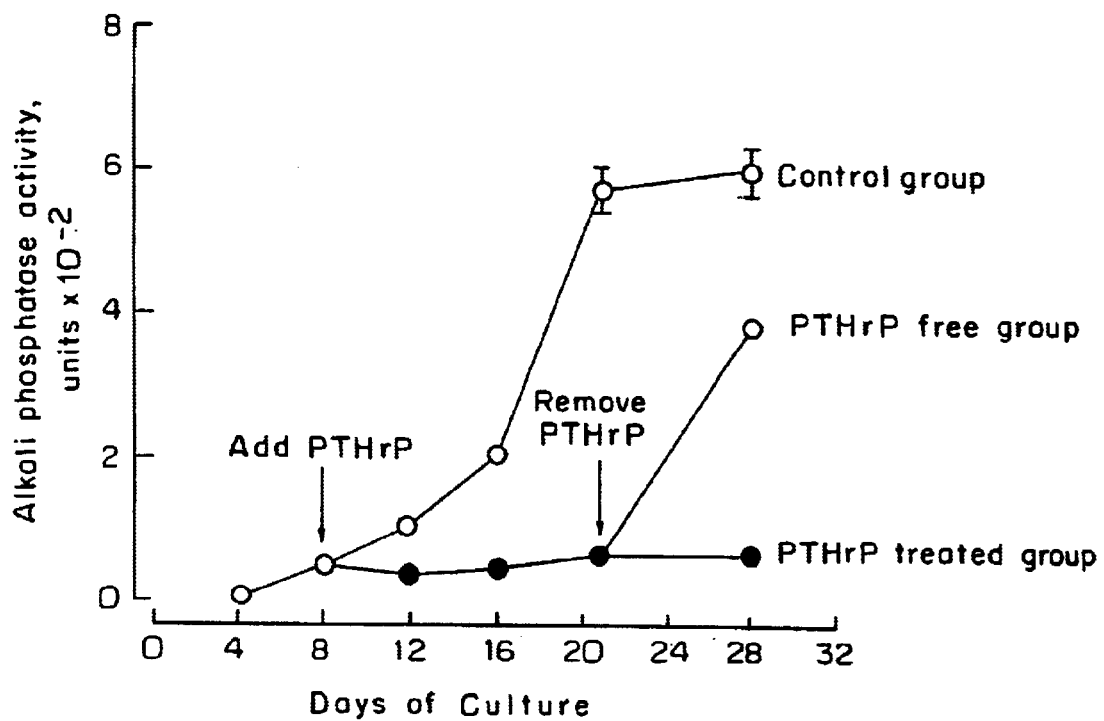
FIG. 5 is a graph showing how the ALP activity of chondrocytes increased over time and how effective PTHrP was in suppressing that phenomenon.
Figure 6:
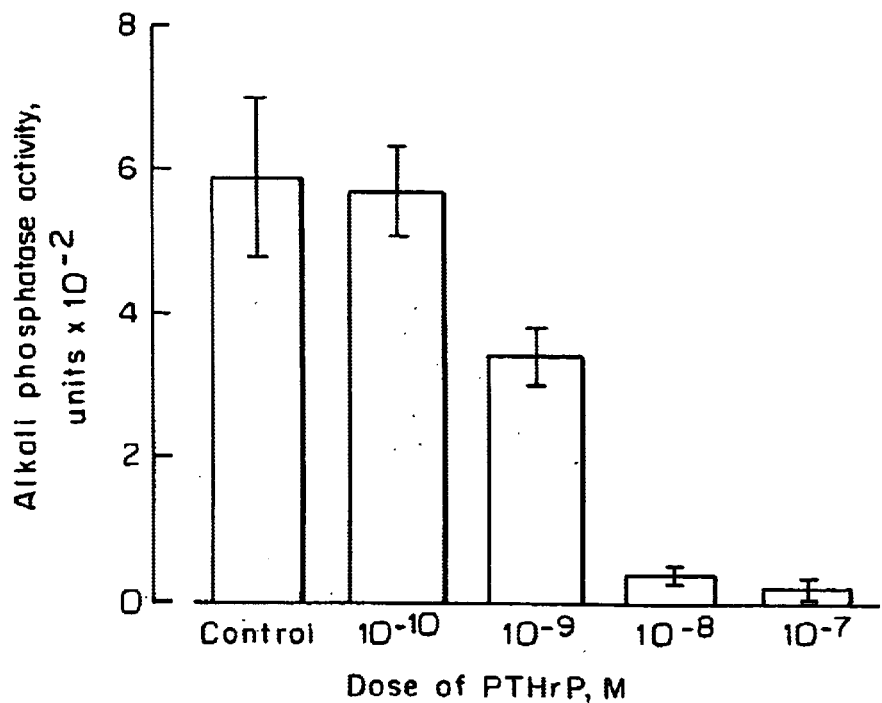
FIG. 6 is a graph showing that PTHrP was effective in controlling the ALP activity in a dose-dependent manner.

FIG. 5 shows the time-dependent effect of PTHrP on the ALP activity, and FIG. 6 shows the dose-response relationship between ALP activity and PTHrP on the 21st day of its addition. Obviously, upon addition of PTHrP, the ALP activity of the chondrocytes was suppressed and this efficacy of PTHrP lasted as long as it was in action (see PTHrP Treated Group in FIG. 5). The effect was reversible and the ALP activity was restored to the level of the control group after the PTHrP was eliminated from the culture solution on the 21st day of the cultivation (see PTHrP Free Group in FIG. 5). The effect was dose-dependent and at concentrations above $10^{-9}$ M, the PTHrP started to suppress the ALP activity and at $10^{-8}$ M, the ALP activity was suppressed almost completely (see FIG. 6).

Figure 7:
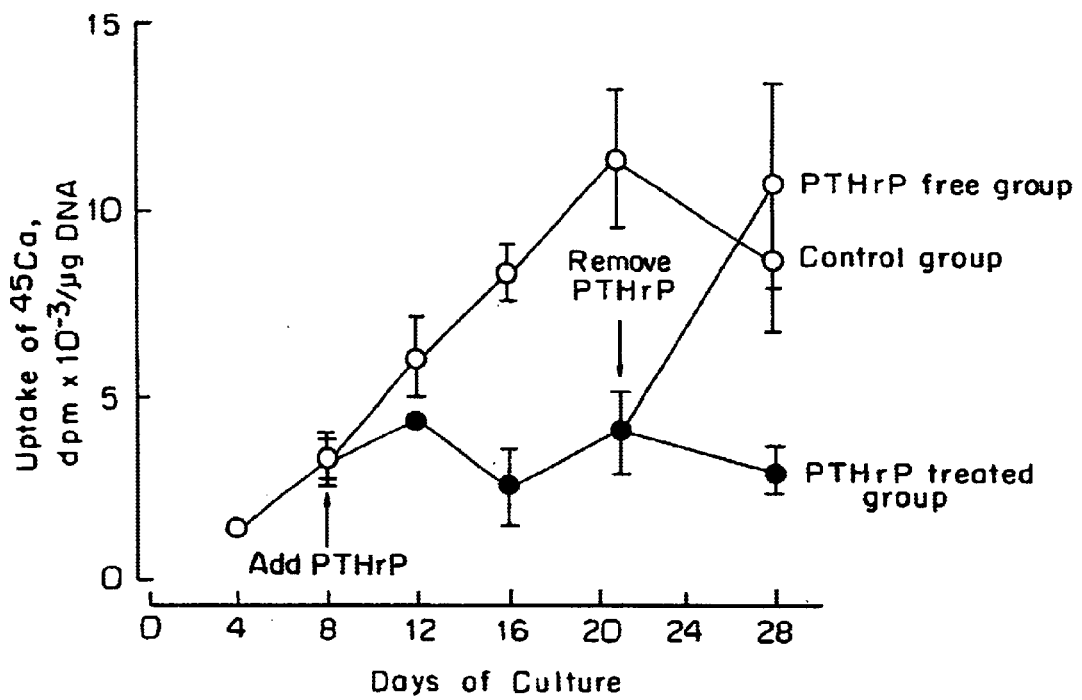
FIG. 7 is a graph showing the ability of chondrocytes to become calcified over time and how effective PTHrP was in suppressing that phenomenon.
Figure 8:
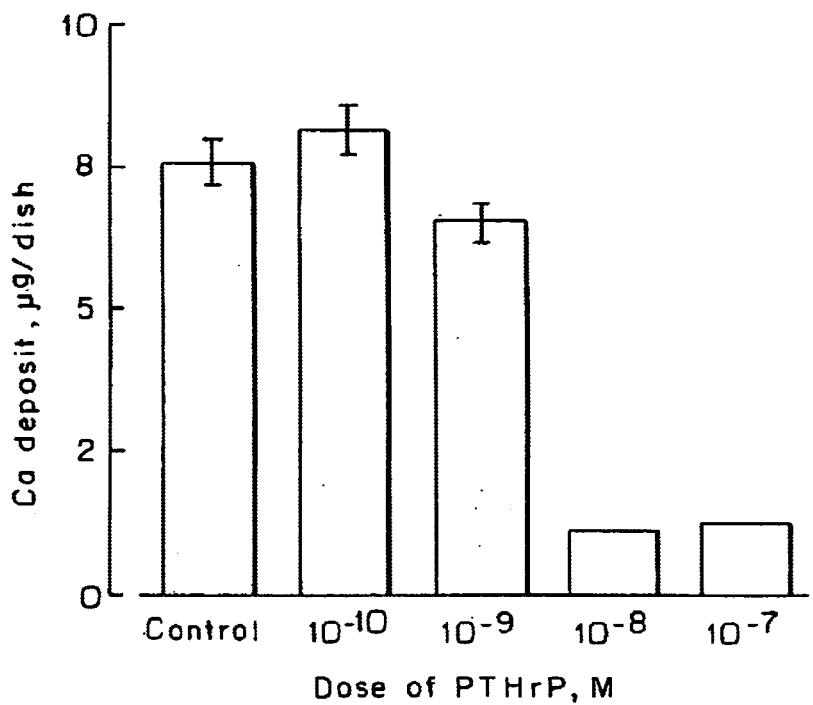
FIG. 8 is a graph showing that PTHrP was effective in controlling calcification in a dose-dependent manner.

The PTHrP also suppressed ensuing the calcification. At $10^{-7}$ M. PTHrP suppressed the incorporation of $^{45}Ca$ into the chondrocytes (see PTHrP Treated Group in FIG. 7) and this effect soon disappeared when the PTHrP was removed (see PTHrP Free Group in FIG. 7). The calcification suppressing action of PTHrP was dose-dependent and at concentrations higher than $10^{-8}$ M, the calcification of chondrocytes was completely suppressed (see FIG. 8). These results show that PTHrP is effective as a therapeutic of osteoarthritis.

Example 5

As in Example 1, grown chondrocytes were separated from the subchondral bone to bone transition area of rabbits 4 weeks old from birth by the method of Shimomura et al. (Shimomura, Y. et a., Calcif. Tissue Res. 19, 179–187, 1975). The separated chondrocytes were suspended in an Eagle's minimum essential medium (MEM) containing 10% fetal bovine serum and 50 μg/mL of ascorbic acid and seeded on a 3.5-cm Petri dish coated with type I collagen, each well containing 5,000 cells. Following 30-day cultivation, $10^{-8}$ and $10^{-7}$ M of PTHrP was brought into action for the last 6 days. RNA was prepared from the cultured cells by the CsTFA method (Smale and Sasse, Anal. Biochem. 203, 352–356. 1992), separated by electrophoresis and thereafter transferred onto a membrane. The membrane onto which the RNA had been transferred was hybridized with a $^{32}P$ labelled cDNA probe for type X and II collagens.

Figure 9:
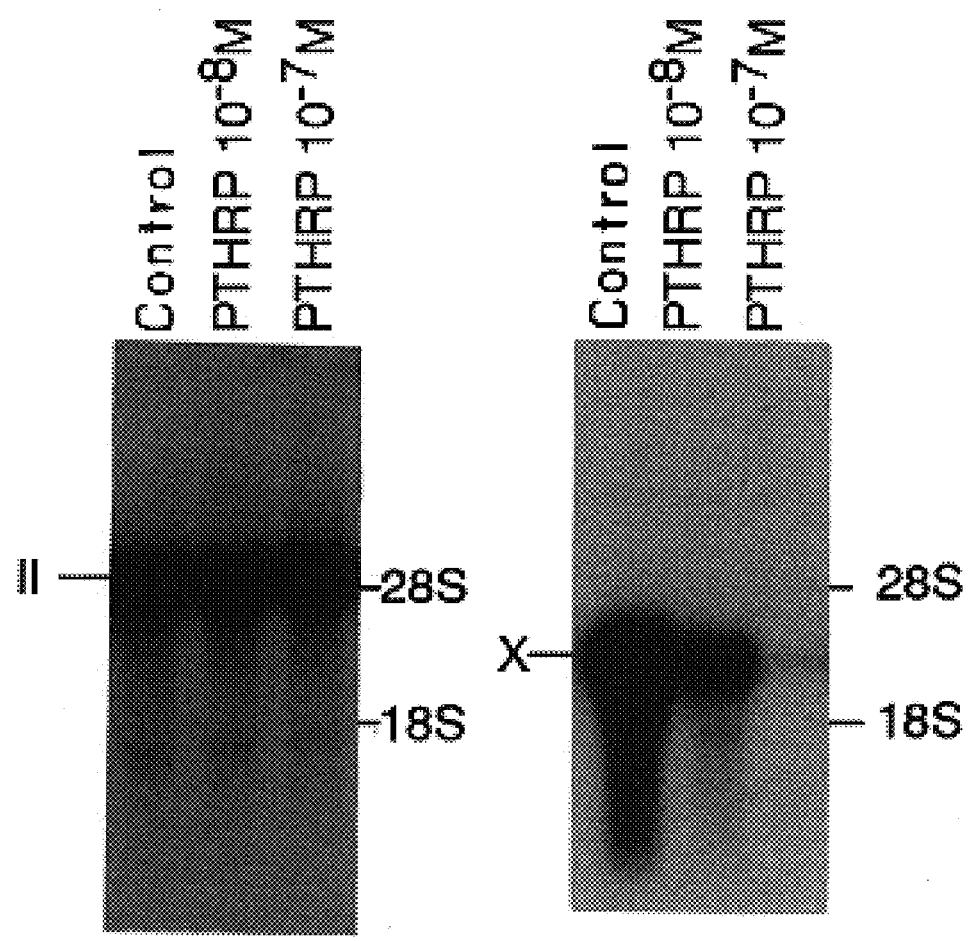
FIG. 9 is a set of electropherograms showing the effect of PTHrP on the expression of the mRNA of type X and II collagens.

The results are shown in FIG. 9; the left electropherogram visualizes the expression of the mRNA of type II collagen and the right electropherogram shows the expression of the mRNA of type X collagen. Obviously, PTHrP had no effects on the expression of the mRNA of type II collagen when it was added at a concentration of $10^{-8}$ or $10^{-7}$ M; on the other hand, the PTHrP significantly inhibited the expression of the mRNA of type X collagen in a dose-dependent manner. These findings show that PTHrP specifically suppresses the expression of the mRNA of type X collagen which is closely involved in calcification (i.e., strongly suppressed the calcification of the cartilage) but that the production of type II collagen which is a matrix component is not affected adversely.

Industrial Applicability

The drug of the invention which contains PTHrP as an effective ingredient is useful not only in preventing diseases such as osteoarthritis that involve the destruction and degeneration of articular cartilage tissue but also providing for an etiotropic and direct therapy of such diseases.

What is claimed is:

1. A method for suppressing the incorporation of calcium into chondrocytes or the calcification of cartilage and subchondral bone, comprising administering to a patient suffering from a disease that involves the destruction and degeneration of articular cartilage tissue, a therapeutically effective amount of a parathyroid hormone related peptide (PTHrP) or a PTHrP derivative substance comprising amino acids 1–34 of PTHrP.

2. The method according to claim 1, wherein said disease that involves the destruction and degeneration of articular cartilage tissue is osteoarthritis.

3. A method for suppressing the formation of type X collagen in cartilage, subchondral bone or chondrocytes, comprising administering to a patient suffering from a disease that involves the destruction and degeneration of articular cartilage tissue, a therapeutically effective amount of a parathyroid hormone related peptide (PTHrP) or a PTHrP derivative substance comprising amino acids 1–34 of PTHrP.

4. The method according to claim 3, wherein said disease that involves the destruction and degeneration of articular cartilage tissue is osteoarthritis.

5. A method for suppressing the alkali phosphatase activity in cartilage, subchondral bone or chondrocytes, comprising administering to a patient suffering from a disease that involves the destruction and degeneration of articular cartilage tissue, a therapeutically effective amount of a parathyroid hormone related peptide (PTHrP) or a PTHrP derivative substance comprising amino acids 1–34 of PTHrP.

6. The method according to claim 5, wherein said disease that involves the destruction and degeneration of articular cartilage tissue is osteoarthritis.

* * * * *